United States Patent
Find

(10) Patent No.: US 6,897,065 B1
(45) Date of Patent: May 24, 2005

(54) METHOD FOR MATURATION OF CONIFER SOMATIC EMBRYOS

(75) Inventor: Jens Iver Find, Rotorua (NZ)

(73) Assignee: Woody Plant Biotech APS, Lundby (DK)

( * ) Notice: Subject to any disclaimer, the term of this patent is extended or adjusted under 35 U.S.C. 154(b) by 40 days.

(21) Appl. No.: 10/088,236

(22) PCT Filed: Sep. 20, 2000

(86) PCT No.: PCT/DK00/00522

§ 371 (c)(1),
(2), (4) Date: Jun. 19, 2002

(87) PCT Pub. No.: WO01/20972

PCT Pub. Date: Mar. 29, 2001

Related U.S. Application Data

(60) Provisional application No. 60/161,938, filed on Oct. 28, 1999.

(30) Foreign Application Priority Data

Sep. 21, 1999 (EP) .............................................. 99203104

(51) Int. Cl.⁷ ............................. C12N 5/04; C12N 5/02; A01H 7/00
(52) U.S. Cl. ...................... 435/422; 435/430.1; 435/430
(58) Field of Search ............................. 435/422, 430.1, 435/430

(56) References Cited

U.S. PATENT DOCUMENTS

| 5,187,092 A | 2/1993 | Uddin |
| 5,413,930 A * | 5/1995 | Becwar et al. ............... 435/422 |
| 5,565,355 A | 10/1996 | Smith |

FOREIGN PATENT DOCUMENTS

| GB | 1 387 821 | 3/1997 |
| JP | 19950282376 | 4/1997 |
| WO | WO 93/11660 | 6/1993 |
| WO | WO 96/37096 | 11/1996 |
| WO | 9723126 | 7/1997 |

OTHER PUBLICATIONS

Kebebew et al, Plant Cell Reports (1998) 18: p 154–158 Nov. 1998.*

XP002153913, Abstract, 1987, Hormonal control of organogenesis and somatic embryogenesis in beta–vulgaris callus; Tetus T et al Journal of Experimental Botany, vol. 38, No. 188, 1987, pp. 506–517, Database Biosis.

(Continued)

Primary Examiner—Bruce R. Campell
Assistant Examiner—Louanne Krawczewicz Myers
(74) Attorney, Agent, or Firm—Iver P. Cooper

(57) ABSTRACT

According to the invention an embryogenic cell mass is cultured with a culture medium comprising an anti-auxin resulting in an unexpected shift in physiology from proliferation to maturation. Proliferation is reduced so that the formation of new immature embryos ceases. Reduction of proliferation facilitates the transition from proliferation to maturation and maturation frequency is increased to a much larger extend than expected. Surprisingly, it has been discovered that the quality of the somatic embryos is not reduced, although the activity of the important endogenous plant growth regulator, auxin, is reduced. As a mater of fact, the overall quality of the mature embryos harvested at the end of maturation is actually increased over the prior art.

26 Claims, 9 Drawing Sheets

OTHER PUBLICATIONS

Figure 1:
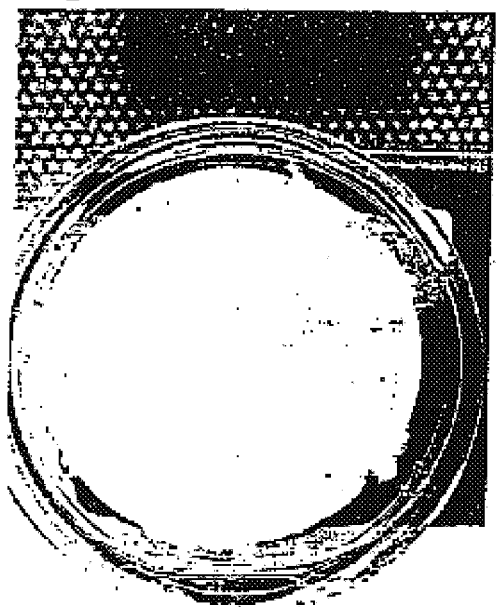
Figure 1:
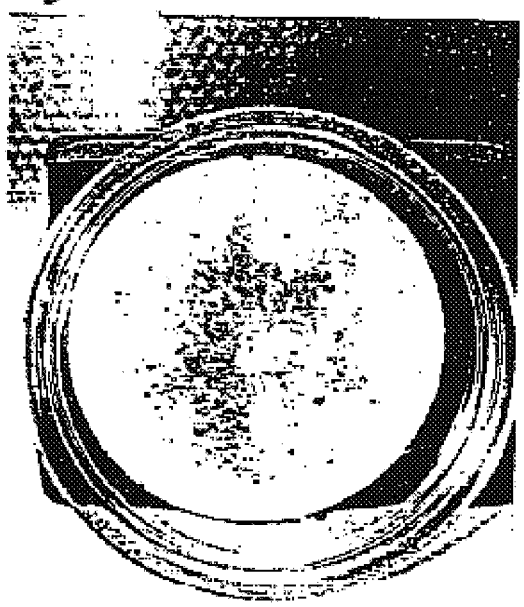
Figure 1:
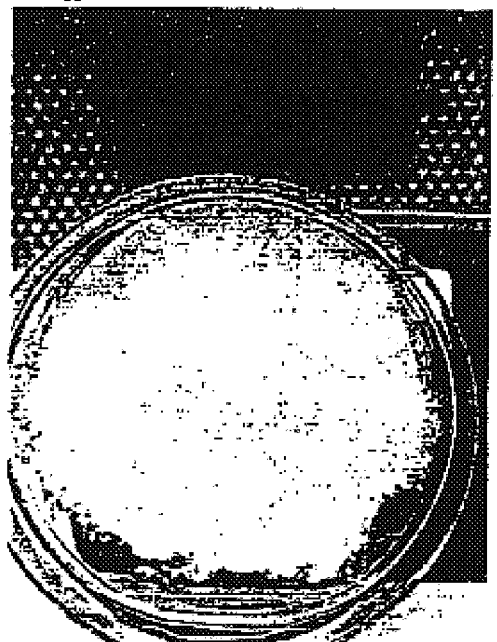
Figure 1:
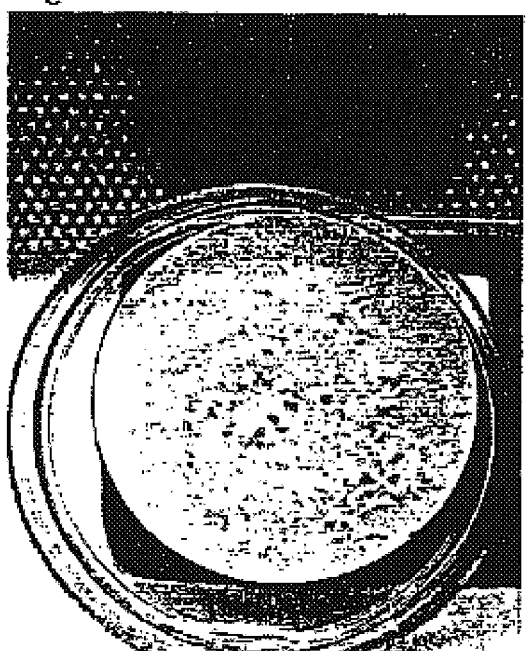

XP002153914, Abstract, 1984, Embryogenesis inhibition and simulation in oil palm callus derived from leaf explants; Hanower J et al Comptes Rendus des Seances de l'Academie des Sciences Serie III Sciences de la Vie, vol. 298, Database Biosis.

XP002153915, Abstract, 1976, The effect of the anti auxin p chlorophenoxy iso butyric–acid on the formation of meristematic centers during regneration of isolated tissue fragments of riella–helicophylla; Grotha R Planta (Heidelberg), vol. 129, No. 3, 1976, pp. 235–238 Database Biosis.

1996, Boron controls suspensor development in embryonic cultures of Larix decidua Ulrike Behrendt; Kurt Zoglauer Phsiologica Planterum, 97, 321–326.

1979, Involvement of Endogeneou Auxin in Somatic Embryogenesis in a Carrot Cell Suspension Culture Tatsuhito Fujimura; Atsushi Komamine Z. Pflanzenphysiol, 13–19.

1993, Inhibition by 2,4–D of somatic embryogenesis in carrot as explored by its reversal by difluoromethylornithine Per Nissen; Subhash C. Minocha Physiologia Planterum, 89, 673–680.

1984, Embryogenesis Inhibition and Stimulation in Oil Palm Callus Derived from Leaf Explants Janina Hanower; Paul Hanower C.R. Acad. Sc. Paris, t. 298, Serie III, No. 2, 1984.

1997, Somatic embryo maturation and plant regeneration in Ables nordmanniana Lk Jens Viktor Nørgaard Plant Science 124, 211–221.

1989, Synchronous and High frequency germination of interior spruce somatic embryos following partial drying at high relative humidity D.R. Roberts et al Forest Biotechnology Centre, British Columbia Reserach Corporation.

Abscisic acid and indole–3–butyric acid regulation of maturation and accumulation of storage Dane R. Roberts et al Phsyiologia Planterum 78: 355–360.

* cited by examiner

METHOD FOR MATURATION OF CONIFER SOMATIC EMBRYOS

This application is the national stage of PCT/DK00/00522, filed Sep. 20, 2000, published in English, which claims benefit of 60/161,938, filed Oct. 28, 1999.

TECHNICAL FIELD

The invention relates to the field of methods for plant propagation by tissue culture techniques, more particularly for plant propagation of coniferous trees by somatic embryogenesis.

PRIOR ART

Due to the very long generation cycles in conifers in general, breeding through crossing and selection proceeds very slowly and due to the fact that conifers are notorious outbreeders the offspring of even highly selected individuals varies enormously. However, through clonal propagation, it is possible to capture both the additive and the non-additive variation within a population whereby additional genetic gain is obtained. For a number of economically important conifers, methods have been developed for clonal propagation mainly as rooted cuttings, but for the vast majority of these species, sexual propagation via seeds is the only or the only cost-effective method for propagation.

Even in the cases, where methods for propagation via cuttings have been developed, the outcome is often not satisfactory, since rooting percentage declines with the age of the mothertree, and since there is a tendency for plagiotropic growth of cuttings not taken from the apical shoot. For these reasons there is a tremendous world-wide interest in developing cost-effective methods for reproducible clonal propagation of conifers.

The advent of genetic transformation as a tool for breeding of trees also necessitates the development of efficient and reproducible methods for regeneration of plants from transformed tissue. It is imperative that the regeneration methods are applicable to almost all cell lines in order to avoid any unintentional selection during the propagation step succeeding the transformation step.

In short, plant regeneration through somatic embryogenesis in conifers consists of a number of consecutive steps. First, an embryogenic culture is initiated from an explant, which could be either an embryo, mature or immature, a seedling, or recently also buds from adult trees (WO 99/23874 AFOCEL). This step is carried out on any suitable plant culture medium containing various plant growth regulators largely depending on the genus of the species in question. Typically, both auxin and cytokinin are included, but there are also reports on initiation using only cytokinin (Nørgaard & Krogstrup 1995, p 344, Table 1) or even initiation without any plant growth regulators (U.S. Pat. No. 5,565,355 NEW ZEALAND FOREST RESEARCH INSTITUTE, Nørgaard & Krogstrup 1995, page 345).

For continued proliferation, the initiated cultures are either subcultured on medium with the same composition as the induction medium or they are subcultured on medium with lower concentrations of plant growth regulators. At this stage, the proliferating cell masses consist of more or less well differentiated immature somatic embryos, which morphologically correspond to a stage found in the developing seed in the early phase of seed development under optimal conditions, the somatic embryos do not undergo any further development during proliferation and mature embryos are thus not formed during this phase.

In order to obtain embryo maturation, the cultures need to be transferred to a plant culture medium, where—typically—auxin and cytokinin are omitted and abscisic acid (ABA) is included. In some cases, a short (1–2 weeks) transition step is included, during which the cell masses are cultured on plant culture medium devoid of plant growth regulators and sometimes including activated charcoal. This phase is believed to facilitate subsequent maturation, due to the lower content or absence of auxin and cytokinin in the culture medium and their possible removal by activated charcoal. A doubling of the subsequent maturation frequency has been reported (WO93/11660).

A number of factors have been shown to have a general stimulatory effect on the frequency of embryo maturation and/or on the quality of the mature embryos formed. The most important factor is the naturally occurring plant growth regulator abscisic acid. Today, this compound or analogues or derivatives thereof are included in almost all protocols for maturation of conifer somatic embryos.

Another factor of importance for the maturation process is the osmolality of the plant culture medium (WO 93/11660 UNIVERSITY OF SASKATCHEWAN). Increasing this by adding a non-permeating osmoticum such as PEG-4000 (Polyethyleneglycol-4000) has been shown to improve especially the quality of the mature embryos. The improvement is suspected to be caused by an increased level of triacylglycerides in the mature embryos. Triacylglycerides are deposited in the cells during maturation of zygotic embryos and are used as an energy source for the germination. PEG-4000 or similar compounds are routinely incorporated into maturation media.

In the vast majority of conifers, sucrose is used as the sole carbohydrate source for the maturation step. However, there are reports that especially maltose may give superior results. This has been reported for Pinus spp (U.S. Pat. No. 5,187,092 INSTITUTE OF PAPER SCIENCE AND TECHNOLOGY) and for *Abies nordmanniana* (Plant Science vol 124:211–221, NØRGAARD).

There are also reports that the inclusion of an auxin into the maturation medium, may stimulate both the number of mature somatic embryos formed, and their quality. U.S. Pat. No. 5,187,092 INSTITUTE OF PAPER SCIENCE AND TECHNOLOGY discloses the use of 0.5–2.0 $\mu$M IBA+10–40 $\mu$M ABA for the maturation of *Pinus taeda* and *Pseudotsuga menziesii* somatic embryos and Roberts et al (1990) discloses the use of 0.1–10 $\mu$M IBA+40 $\mu$M ABA for the maturation of *Picea glaucaxengelmanil*. Thus, it has been shown for very diverse species from three different genera, that the inclusion of an auxin during maturation improves the process.

As pointed out in WO 96/37096 (CARTER HOLT HARVEY LTD.) the percentage of initiated cell lines that are able to form mature embryos is typically 1–10%. WO 96/37096 mentions percentages up to 25% obtained with selected embryogenic cell lines. If these methods are to be used for mass propagation and be combined with breeding in forestry or horticulture, it is of utmost importance that essentially no or very limited selection takes place in the propagation step. Valuable clones may be lost, if it is not possible to propagate them.

In *Picea abies* it has been possible to divide cell lines into two groups based on their morphology and the ability of the cell lines to produce mature somatic embryos. Cell lines capable of producing mature somatic embryos are termed A-type cell lines and they readily produce mature embryos when subjected to known maturation methods with abscisic acid. On the other hand, approximately 50% of all cell lines can be characterised as B-type cell lines, which do not readily produce mature somatic embryos (von Arnold et al 1995).

Another problem associated with the methods of the prior art is the lack of reproducibility.

In many species, proliferation during the maturation phase is a problem. When proliferation continues during maturation, the latter process is inhibited and in many cases the maturing embryos are overgrown by proliferating tissue. In the species belonging to Picea, Pinus and Larix, proliferation does not continue to the same extent as in species belonging to Abies, but may still constitute a problem. Maturing embryos are primarily formed at the edge of the cell mass, i.e. either at its periphery and on top of the cell mass. Embryos formed at the periphery are in contact with the maturation medium and normally achieve a satisfactory quality in terms of morphology and accumulation of storage nutrients. Embryos formed on top of a proliferating cell mass are only in indirect contact with the maturation medium and are also affected by compounds (e.g. growth regulators) exudated or leaked from the proliferating cells. Often the consequence of this is delayed maturation, hyperhydricity, incomplete morphology (e.g. typically malformed or missing cotyledons), and decreased accumulation of storage nutrients.

Finally, it is known that the ability of established embryogenic cultures to undergo maturation declines with their age. For some species, especially the members of Pinus genus the decline is very rapid, i.e. within months. Cultures from several other genera such as Picea, Larix and Abies are more long-term stable, but in most cases, some sort of decline is observed either as a reduced maturation frequency or as a requirement for longer maturation periods or higher concentration of maturation agents such as abscisic acid.

SUMMARY OF THE INVENTION

In a first aspect of the invention a method is provided for maturation of conifer somatic embryos, comprising a step, where an embryogenic cell mass is cultured with a culture medium comprising an anti-auxin.

By including an anti-auxin in the culture medium during at least part of the maturation, several unexpected and positive effects are obtained.

Proliferation is reduced. This means that the formation of new immature embryos ceases. Reduction of proliferation in itself facilitates the transition from proliferation to maturation. But maturation frequency is increased to a much larger extent than expected merely from the reduction in proliferation. The anti-auxin results in an unexpected shift in physiology from proliferation to maturation.

Almost all embryogenic cell lines tested, irrespective of the species, respond to the maturation treatment with production of mature somatic embryos. Thereby, a much higher maturation percentage than experienced by the prior art is obtained.

Surprisingly, it has been discovered that the quality of the somatic embryos is not reduced, although the activity of the important endogenous plant growth regulator, auxin, is reduced. As a matter of fact, the overall quality of the mature embryos harvested at the end of maturation is actually increased over the prior art.

The other components of the culture medium such as nutrients, vitamins, osmotica, organic nitrogen, gelling agent, carbon sources and plant growth regulators are not part of the inventive idea according to claim 1. The choice of the skilled person provides an infinite number of possibilities. The prior art contains numerous examples of suitable combinations of macro-nutrients and micro-elements (see e.g. George 1993) as well as suitable metabolisable carbon sources such as for instance sucrose, maltose, lactose, fructose, glucose, maltotriose, starch, galactose etc. In addition to these the person skilled in the art may chose to incorporate vitamins and various sources of organic nitrogen such as amino acids or complex mixtures of these such as casein hydrolysate or other hydrolysates in the culture medium. Furthermore it may be advantageous to include an osmoticum, such as a non-permeating osmoticum such as for instance polyethylene glycols, dextrans, celluloses, pectins, galactans, ficolls, polypropylene glycols, agars, gums, oligosaccharides, proteins, amino adds, polyamino acids, lipoproteins, nucleotides, oligonucleotides, lipopolysaccharides, or permeating osmotic such as for instance polyethylene glycols, sugar alcohols, sorbitol, mannitol, and carbohydrates. The culture medium used during the various steps of maturation may be either liquid, the cells being cultured in the medium or in contact with the medium on some sort of solid phase support. Alternatively the medium may be gelled with one or more of the known gelling agents such as for instance gelrite, phytagel, agar, agarose, starch or similar agents. Irrespective of the culture medium, the cells may be cultured on a filter paper or similar support means, which facilitates subculture significantly.

Finally the culture medium used during maturation may comprise additional plant growth regulators such as cytokinins, gibberellins, or even auxins.

In the case, where one of the steps according to the invention is relatively short, e.g. less than 3 weeks, the culture medium may be very simple excluding one or all the groups of traditional medium components. The culture medium may also simply be water or gelled water, since the embryogenic cell mass may easily survive a period without nutrients and/or metabolisable carbon.

The length of the step comprising an anti-auxin is preferably between 2 days and 50 weeks, the length depending on the species and the specific cell line in question. Experiments have shown that whereas some cell lines should be cultured on medium with anti-auxin during the whole maturation period, other cell lines only require 24 weeks or even less to obtain the effects mentioned above. Similarly, the age of the cell line has a pronounced effect of the total length of the maturation period, younger cell lines such as less than one year old generally maturing much faster than old cell lines such as more than five years old. Thus, younger cell lines would normally also require a shorter period of exposure to anti-auxin. A sign of too long exposure to the anti-auxin is the appearance of malformed embryos with irregular or missing cotyledons. In this case the period of exposure to anti-auxin should be shortened.

Preferably the method further comprises a second step before the anti-auxin step, where the embryogenic cell mass is cultured with a culture medium. For the majority of species and cell lines, an exposure to anti-auxin right from the beginning of maturation has turned out to reduce the viability of the plated cells. This is partly due to the fact that newly plated cells are in a stressed condition and the culture needs to be "established" on the maturation medium before exposure to anti-auxin. The length of the second step before the anti-auxin step is advantageously between two days to 10 weeks.

Often it is likewise preferable to include a third step after the anti-auxin step where the embryogenic cell mass is cultured with a culture medium essentially free of anti-auxin. As mentioned above, a too long exposure to anti-auxin may have undesirable side-effects in which case the culture with maturing embryos has been transferred to a culture medium devoid of anti-auxin but including all other necessary components for continued maturation. Preferably the third step after the anti-auxin step lasts from two days to 40 weeks.

Unexpectedly, the shift of the addition of a metabolisable carbon source such as from maltose to sucrose in the culture medium in the third step omitting the anti-auxin gave a surprising positive maturation effect of the size of the mature embryos, the appearance of the embryos and shortening of the maturation period.

In a preferred embodiment of the invention, the culture medium in at least one of the steps also contains a maturation agent. Whereas embryo maturation is possible without the use of any maturation agent, it has been determined that the addition of such an agent to the culture medium increases the maturation frequency and the quality of the embryos greatly. Depending on the length of the various phases, the maturation agent may be present during one, two or all three steps. Preferably the agent is present during all three steps.

Preferably, the maturation agent is selected from the group comprising abscisic acid, silver nitrate, jasmonic acid, abscisyl alcohol, acetylenic aldehyde, dihydroacetylenic alcohol, phaseic acid, dihydrophaseic acid, 6'-hydroxymethyl abscisic acid, beta-hydroxy abscisic acid, beta-methylglutaryl abscisic acid, beta-hydroxy-beta-methylglutarylhydroxy abscisic acid, 4'-desoxy abscisic acid, abscisic acid beta-D-glucose ester, 2-2(2-p-chlorophenyl-trans-ethyl)cyclopropane carboxylic acid. These agents have been shown to promote maturation or are analogues or derivatives of such agents.

More preferably, the maturation agent is abscisic acid, which has been shown to promote maturation especially well. The concentration of abscisic acid in the culture medium is preferably between 0.1 and 200 $\mu$M.

The inventive idea of the present invention encompasses all methods for reducing the effect of auxin during the maturation period. This can be done by adding compounds with anti-auxin function such as compounds causing auxin-degradation, compounds inhibiting the auxin-effect, compounds causing auxin-inactivation, compounds inhibiting the synthesis of auxin, or compounds inhibiting auxin-transport. Another way to inhibit or reduce the effect of auxin is to omit compounds that are necessary for auxin synthesis, such as for instance boron or zinc or omission of compounds in the biosynthesis pathway leading to auxin, such as tryptophan.

The anti-auxins according to the invention include but are not limited to the following compounds as well as analogues and derivatives thereof: $\alpha$-(1-naphtylmethyl-sulfide)-isobutyric acid, $\alpha$-(1-naphtylmethyl-sulfide)-propionic acid, $\alpha$-(2-naphtylmethyl-sulfide)-isobutyric acid, $\alpha$-(2-naphtylmethyl-sulfide)-propionic acid, $\delta$-(naphtylmethyl-selenide)-$\eta$-valeric acid, (−)-$\alpha$-(2,4,5-trichlorophenoxy)-propionic acid, (−)-$\alpha$-(2,4-dichlorophenoxy)-propionic acid, (−)-$\alpha$-(2-naphthoxy)-propionic acid, (+)-$\alpha$-(1-naphthoxy)-propionic acid, (3-phenyl, 1,2,4-thiadiazol-5-yl)thioacetic acid (PTAA), $\beta$-naphthalene acetic acid ($\beta$-NAA), $\gamma$-phenylbutyric acid, 1-(naphthylmethyl-sulfide)-propionic acid, 1-naphthylmethyl-selenidacetic acid, 2-(naphthylmethyl-sulfide)-propionic acid, 2-(o-chlorophenoxy)-2-methylpropionic acid, 2,3,4,5,6-pentachlorophenoxyisobutryric acid, 2,3,5-tri-iodobenzoic acid (TIBA), 2,3,5-triiodobenzoic acid, 2,4,5-trichlorophenoxyisobutyric acid, 2,4,6-trichlorophenoxyacetic acid (2,4,6-T), 2,4,6-trichlorophenoxyisobutyric acid 2,4-dichloroanisole (2,4-DCS), 2,4-dichlorophenoxyisobutyric acid (2,4-DCIP), 2,4-dichlorophenylsulfoneacetic acid, 2-4-dichlorophenylsulfoxideacetic acid, 2-6-dichlorophenoxyacetic acid, 2-chlorophenoxyisobutyric acid, 2-naphtylmethyl-selenidacetic acid, 3-chlorophenoxyisobutyric acid, 3-indoleisobutryric acid, 3-nitro-4-flourobenzoid acid, 4-chlorophenoxyisobutyric acid, 5-methyltryptophan, 7-aza-indol, 9-hydroxyfluorene-9-carboxylic acid (HFCA), ferulic acid, flavonoids, indole-isobutyric acid, kaempferol, maleic hydrazide, naptalam (N-1-naphtylphthalamic acid), p-Chlorophenoxyisobutyric acid (PCIB), p-coumaric acid, phenoxyacetic acid, phenoxy-isobutyric acid, phenylpropionic acid, quercitin, trans-cinnamic acid.

An especially preferred anti-auxin is PCIB, which is preferably present during the anti-auxin step in a concentration between 0.01 and 200 $\mu$M. Especially excellent results are obtained with a concentration of PCIB between 1 and 50 $\mu$M.

The inventive idea is generally applicable to all conifers and especially applicable to plant species being a member of the Pinaceae. Within the Pinaceae, especially excellent results according to the invention are obtained within the genera Pinus, Picea, Abies, Larix, and Pseudotsuga.

According to especially preferred embodiments of the invention the conifer is an Abies sp such as *Abies nordmanniana* Lk. According to another especially preferred embodiment of the invention the conifer is a Picea sp such as *Picea abies* L. Karst. or *Picea sitchensis* (Bong.) Carr.

When the conifer is an Abies sp such as *Abies nordmanniana* it is preferable that the anti-auxin is PCIB at a concentration between 1 and 100 $\mu$M. Experimental data show that this is the concentration range required to obtain the effects according to the inventive idea. Too low concentrations do not result in the desired effects.

When the conifer is a Picea sp it is preferable that the anti-auxin is PCIB at a concentration between 0.1 and 50 $\mu$M. Experiments have shown that the concentration of the anti-auxin should be relatively low to obtain the effects according to the inventive idea. If too high concentrations are added in the case of Picea spp. the effect is more or less lethal. One great advantage of the method is that cell lines that will not normally undergo maturation (such as for *Picea abies* the so-called B-type cell lines) will actually produce significant amounts of embryos according to the present invention.

In another embodiment of the invention the culture medium used during at least part of the third step after the anti-auxin step further comprises an auxin. It has been observed in some cases that the elongation of the cells of the maturing embryos may be partially inhibited even after removal from the medium comprising the anti-auxin. By adding an auxin to the medium during the third step of the maturation this problem can be overcome, and elongation proceeds as desired.

The concentration of the auxin in the culture medium is preferably between 0.001 and 100 $\mu$M. The auxin is preferably selected from the group comprising indole acetic acid, indolebutyric acid, naphtalene acetic acid, 2,4-D, 2-naphtyloxyacetic acid (NOA), 4-chloropheboxyacetic acid (4-CPA), 2-methyl-4-chlorophenoxyacetic acid (MCPA), 2,4,5-trichlorophenoxyacetic acid (2,4,5-T), 3,6- dichloroanisic acid (dicamba), 4-amino-3,5,5-trichloropicolinic acid (picloram), othonil, 2-chloro-3(2,3-dichloro-phenyl)-propionitril (CDPPN).

The exact length of exposure to auxin during the third step should be determined experimentally, and may be anything between 2 days and 40 weeks.

In a second aspect of the invention is provided a mature conifer somatic embryo produced by any of the methods described above. In many cases it has not been possible to produce such embryos in large quantities by the prior art. Furthermore, it has very often not been possible to produce the embryos in a predictable and reproducible way.

Preferably the embryo according to the invention has a water content less than 70% expressed on a wet weight basis. By the prior art it has not always been possible to produce mature somatic embryos having a water content below 70%, especially not in the cases where proliferation has been very pronounced during the maturation step. Since proliferation can be controlled according to the invention, it is also possible to prolong the maturation period to allow the embryos to accumulate larger amounts of storage material such as triacylglycerides and storage proteins. The accumulation of storage material has a pronounced effect on the subsequent germination process.

The embryo according to the invention may be transgenic and thereby comprise recombinant DNA sequences, the transformation being carried out in a step prior to maturation. At present, the only way to produce transgenic conifer embryos is by transformation of cells by various known means and subsequent regeneration of plants by somatic embryogenesis. In many cases it has not been possible to produce mature somatic embryos from transformed embryogenic cell masses. Transformation and the subsequent selection procedure expose the embryogenic cell masses to stress and also takes very long time. Therefore, the cell lines often loose their ability to produce somatic embryos during this stage. This is especially a problem with Pinus spp in which the ability to produce mature somatic embryos declines rapidly with age.

A third aspect of the invention concerns a conifer plant produced from an embryo according to the invention. For many conifer species and many cell lines it has not been possible to regenerate plants by the prior art. Using the methods according to the present invention the percentage of species and cell lines from which mature embryos can be produced has been increased significantly. Since the embryos according to the present invention are also of a higher quality, germination of the embryos and hardening and continued growth of the germinated plants has also been improved.

The plants according to the invention may also be transgenic and comprise recombinant DNA sequences.

DETAILED DESCRIPTION

The invention is now described in more details using a number of examples and the following figures:

FIGURES

FIG. 1. Photograph of rapidly growing *Abies nordmanniana* cell line disclosing maturation according to the invention and according to prior methods.

Figure 2:
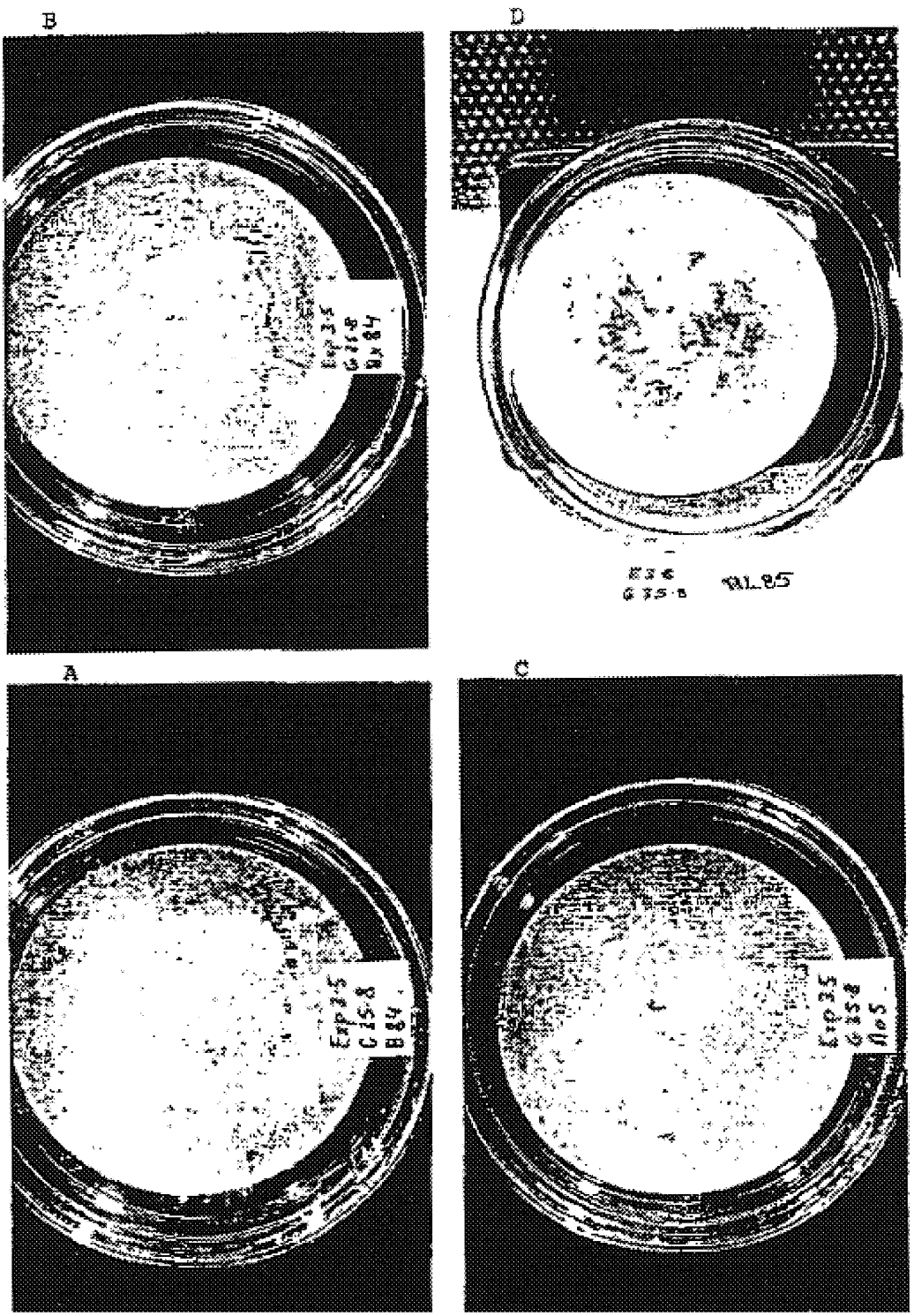

FIG. 2. Photograph of slowly growing *Abies nordmanniana* cell line disclosing maturation according to the invention and according to prior methods.

Figure 3:
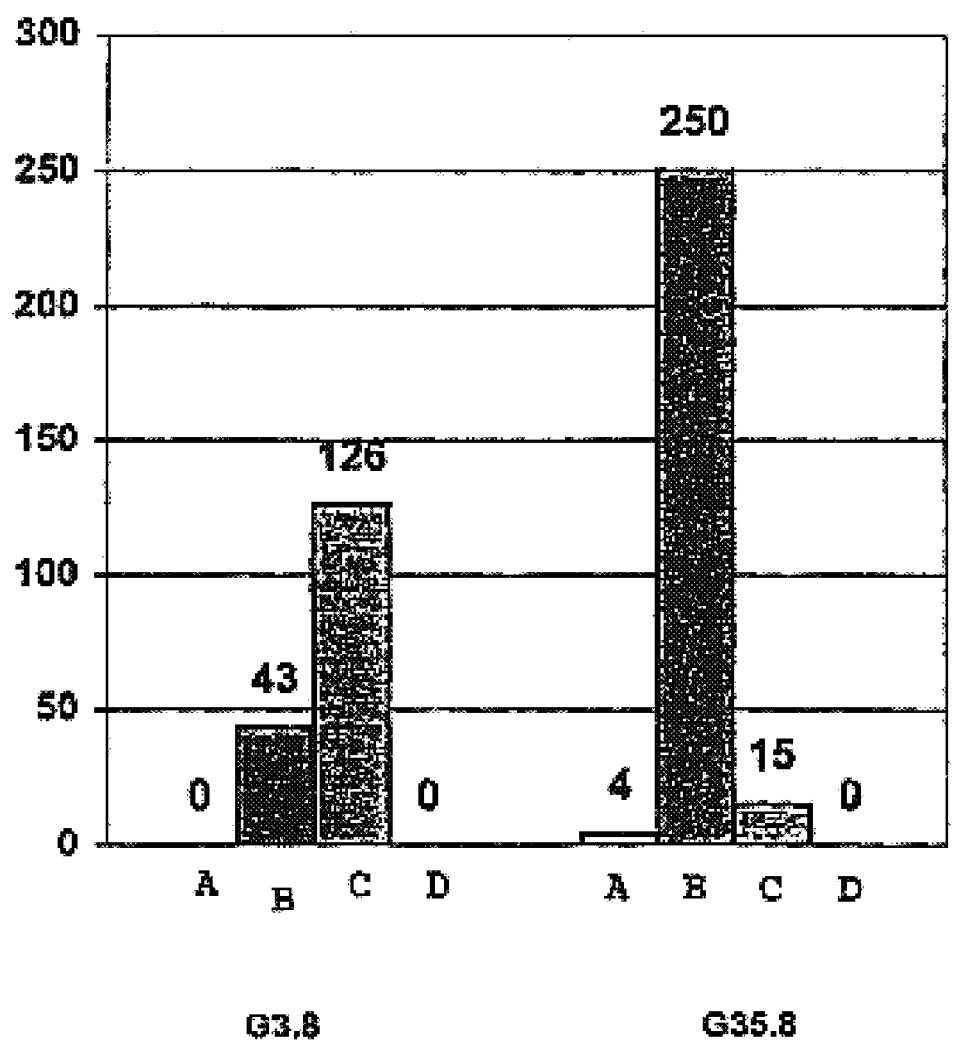

FIG. 3. Graphic illustration of preferred embodiments of the anti-auxin phase according to the invention.

Figure 4:
Figure 4:
Figure 4:
Figure 4:

FIG. 4 Preferred and non-preferred embodiments of an embryo according to the invention.

Figure 5:
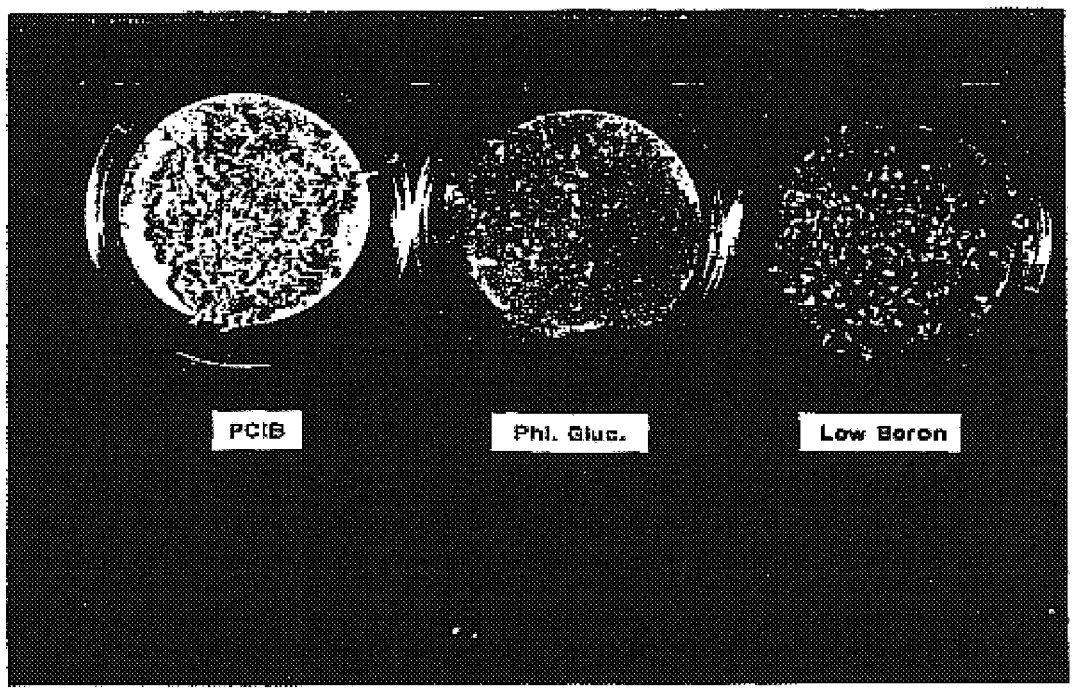

FIG. 5. Photograph of *Abies nordmanniana* cell line matured according to different embodiments of the invention.

Figure 6:
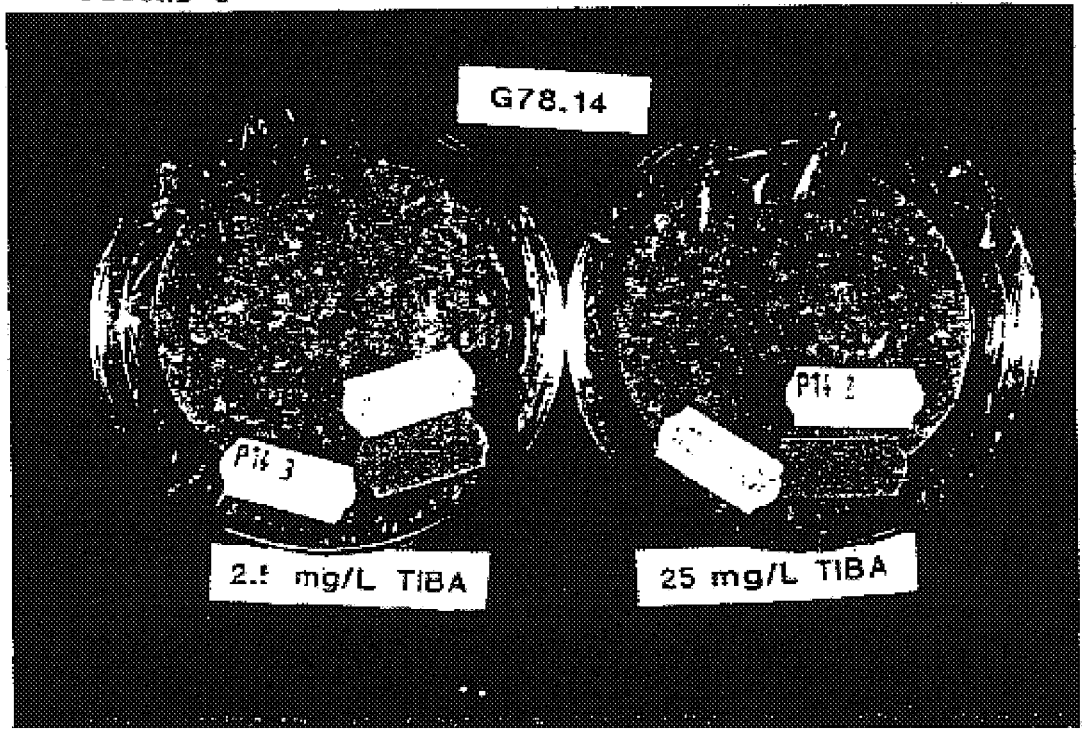

FIG. 6 Photograph of *Abies nordmanniana* cell line matured according to different embodiments of the invention.

Figure 7:
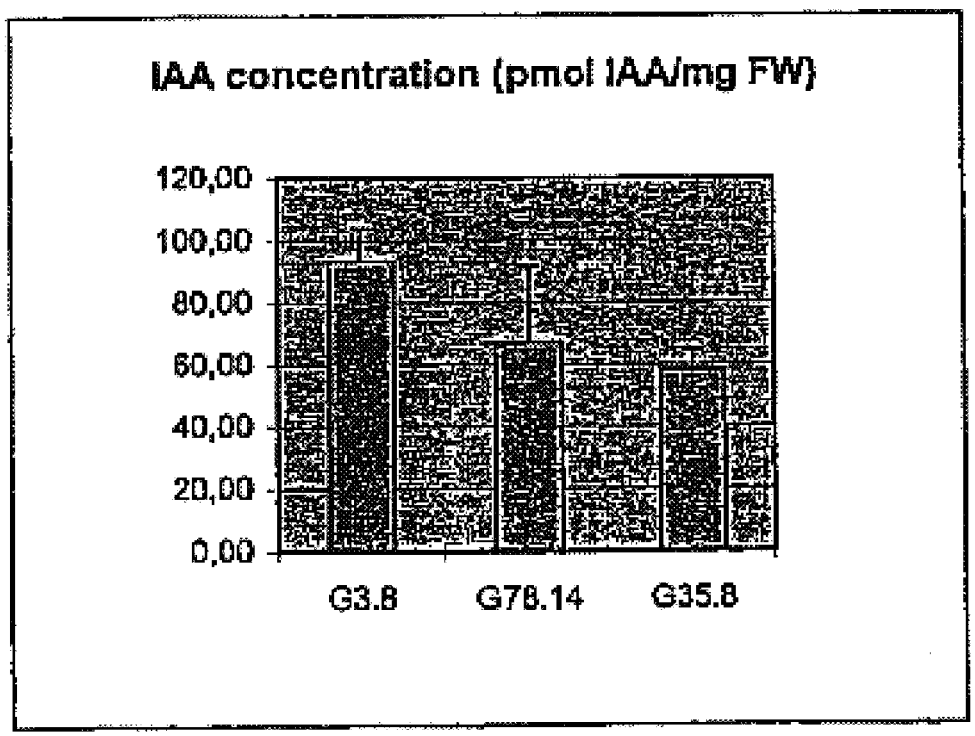

FIG. 7. Graphic representation of the endogenous indole acetic acid (IAA) level in three cell lines of *Abies nordmanniana*.

Figure 8:
Figure 8:
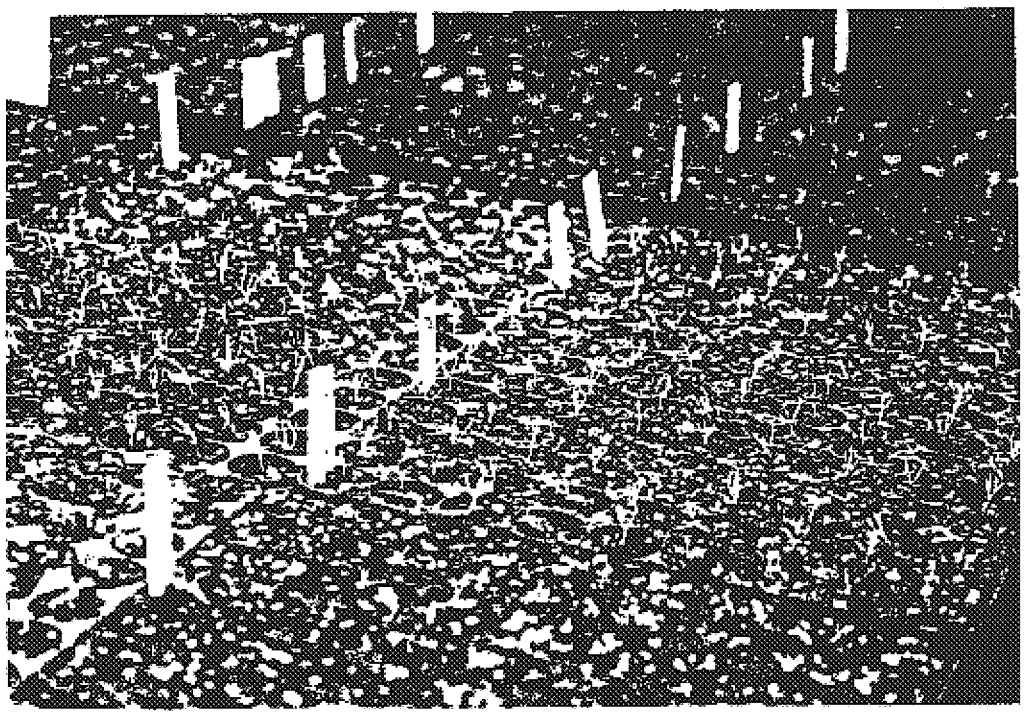

FIG. 8. Photograph of germination and hardening of embryos according to the invention.

Figure 9:
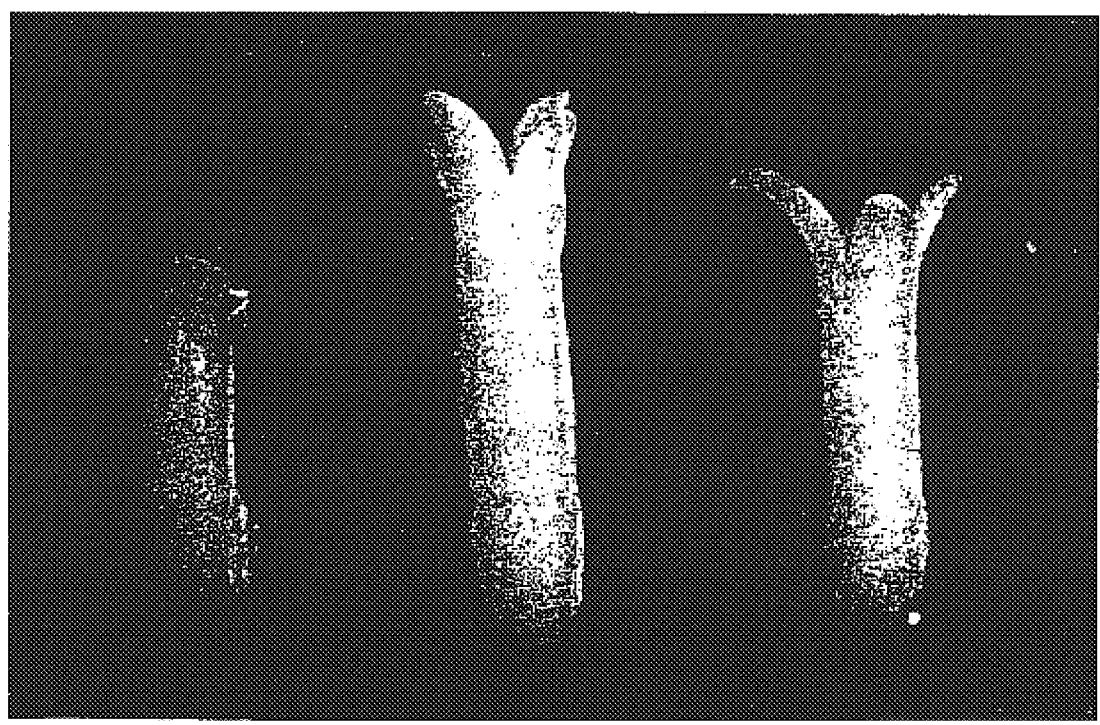

FIG. 9. Photograph of three mature somatic embryos of *Abies nordmanniana*; left picture showing typical embryo from treatment B), center picture showing typical embryo from treatment D), and right picture showing typical embryo from treatment C).

The inventive idea has been tested in a number of different situations, with different conifers and cell lines of various characteristics, such as newly established cell lines and older cell lines, slowly growing cell lines, rapidly proliferating cell lines, transgenic cell lines, cell lines that can produce mature embryos according to known methods (such as A-type cell lines), and cell lines that do not produce mature embryos according to known methods (such as B-type cell lines).

EXAMPLE 1

Maturation in Established Cell Lines of *Abies nordmanniana*

Materials and Methods:

Plant Material

Three different cell lines of *Abies nordmanniana* were used in the present study. The tested cell lines have been in continuous culture for several years. The cell line G.3.8 was initiated from an immature zygotic embryo in 1989 on half strength MS medium (Murashige and Skoog, 1962) as described previously (Nørgaard and Krogstrup, 1991), Cell line G.35.8 was initiated from a mature zygotic embryo on SH medium in 1991 (Nørgaard and Krogstrup, 1995), and cell line G.78.14 was initiated in 1993 from an immature zygotic embryo on modified half strength BLG medium (Verhagen and Wann, 1989). From 1996, all cultures were maintained by biweekly subculture onto fresh half strength modified BLG medium and grown at 24+/−1° C. in the dark. Cell lines G.3.8 and G.78.14 proliferated fast on maintenance medium with a doubling time of the weight shorter than 2 weeks. Cell line G.35.8 proliferated relatively slowly with a doubling time of the weight higher than 2 weeks.

Culture Media for Initiation and Maintenance

The half strength MS medium (Murashige and Skoog, 1962) contained half strength MS macro, micro and FeEDTA. The MS vitamins were modified by 10×thiamine-HCl, 100 mg/l inositol, 500 mg/L L-glutamine and casein hydolysate. The SH medium (Schenck and Hildebrandt, 1972) was modified by inclusion of 500 mg/L l-glutamin and casein hydrolysate. The half strength BLG medium (Verhagen and Wann, 1989) was modified from half strength MS medium by omitting $NH_4NO_3$ and reducing $KNO_3$ to 50 mg/L. KCL was added at 372.5 mg/L, L-glutamine at 750 mg/L and L-aspargine at 50 mg/L. Vitamins were modified by use of 10×thiamine-HCl, 100 mg/L inositol. For all media 1.8 g/L Phytagel (Gellan Gum) was used as gelling agent and pH was adjusted to 5.7 prior to autoclaving. For proliferation, sucrose was used in a concentration of 1% and BAP in a concentration of 5 $\mu$M. No auxin was used in the maintenance medium. The amino acids were prepared as a filter sterilised stock solution and added after autoclaving and cooling of the medium to about 50° C.

Maturation

The standard maturation medium (the control) is modified from the half strength BLG proliferation medium mentioned above. The medium does not include sucrose and BAP, but is supplemented with 45 g/L maltose (Merck 5911), 50 g/L PEG-4000 (Fluka), and 40 $\mu$M ABA (Sigma A1049). The choice of these three culture medium components is determined primarily by the conifer species in question. For *Abies nordmanniana* it is known that superior maturation is achieved by using maltose instead of sucrose as a carbohydrate source. Similarly it is known that addition of PEG-4000 improves maturation. Still it may be possible to obtain just as good results with other combinations of these components and also by using other components with equivalent effects.

Similarly, the half-strength BLG medium has been chosen, because it has been found suitable for many conifers including Abies spp, Picea spp and Pinus spp. An equivalent basal medium may be used to obtain results that are equivalent to the results obtained with BLG medium, the important issue being that the basal medium should be balanced to meet the requirements of the conifer species in question.

In this experiment, the standard maturation medium was modified by excluding PEG and by including one of the following 3 chemicals, that are traditionally expected to affect the endogenous concentration of the naturally occurring auxin IAA or to affect the normal effect of auxin in plant cells: 1) PCIB (auxin-antagonist) in a concentration of 25 or 117 $\mu$M, 2) TIBA (auxin transport inhibitor) in a concentration of 5 or 50 $\mu$M, 3) phlouroglucinol: (inhibitor of auxin degradation) (see George 1993, page 429 bottom–430) in a concentration of 30 mM. In addition to these modifications the standard maturation medium was modified by: 4) reducing the concentration of boron (precursor of indole acetic acid synthesis) to 10 $\mu$M, i.e. 20% of the normal concentration and finally by 5) including 25 $\mu$M PCIB in medium with no ABA.

The cultures were matured in the dark at 24° C.+/−1° C.

The anti-auxins and means to reduce endogenous auxin effects have been chosen to represent different groups of treatments or compounds. Thus the experiment represents very different ways of reducing auxin concentration or reducing auxin effects as well as the necessary controls and a treatment that is expected to increase endogenous auxin concentration.

Plating

Two weeks after the last subculture, 4 grams of embryogenic cells was transferred to a 250 mL Flask (Blue cap) together with a magnet stirrer. 100 mL of liquid proliferation medium was added, and the suspension was stirred for 5 minutes at high speed on a magnet stirrer to obtain a homogenous suspension of cells and cell clumps. The culture was then pre-cultured on a gyrotory shaker (120 rpm) for one week at 24+/−1° C. in the dark. Following the pre-culture, the culture was stirred again on a magnet stirrer at high speed for 5 minutes. The culture was transferred to a 100 mL measuring cylinder and allowed to settle for 30 min. The supernatant was discharged and from the remaining culture aliquots of 1 mL were transferred with a cut pipette tip onto filter paper (Whatmann #2) placed on 25 mL of maturation medium in 10 cm Petri dishes (Nunc, Denmark). The filters containing the maturing somatic cultures were transferred onto fresh medium every 2 weeks.

The purpose of plating the cultures onto the maturation medium is to get an uniform spread of the plated cells on the solid support (in this case filter paper) in order to increase reproducibility and reduce variation. Maturation may also simply be initiated by transferring clumps of embryogenic cell mass to the maturation medium.

Germination

Well-developed mature embryos were collected for cold treatment after about 20 weeks of maturation. The isolated mature embryos were transferred to a nylon filter that was placed on a foam rubber pad in a high Petri dish. A wetted filter paper was placed in the bottom and in the lid of the Petri dish. The Petri dish was closed, sealed with two rounds of polyethylene film, wrapped with aluminium foil, and then placed at 5° C. in the dark for 4 weeks for cold treatment. After cold treatment, the nylon filter with the mature embryos was transferred to BGM-2 medium (Krogstrup et al, 1988). The BGM-2 medium included 20 g/L sucrose, 10 g/L activated charcoal (Merck 5411), and was galled with 3.5 g/L Phytagel (Gellan gum). The Petri dishes were placed in a growth room at 20° C. with a 16 hour photoperiod. After one week of germination, the nylon net was removed and the embryos were placed in direct contact with the medium. After two weeks of germination, embryos with a root were placed vertically with the root submerged in the medium. Later, the germinating embryos were transferred to soil and placed in a controlled greenhouse.

The described method for germination is just one of many different methods that can be used to germinate conifer somatic embryos. Thus, it may also be found advantageous to include a desiccation step between the embryo maturation and germination. During this step the embryo may be subjected to controlled desiccation in order to simulate the maturation drying taking place during the corresponding last phase of seed maturation.

Water Content

The water content of mature somatic embryos and embryos from seeds was measured by weighing approximately 25 embryos (fresh weight, FW), drying the embryos at 60° C. for two days and weighing the embryos again (dry weight, DW). The water content is the calculated on a fresh weight basis: (FW−DW)/FW.

Results:

FIGS. 1 and 2 disclose maturation of two embryogenic cell lines of *Abies nordmanniana*. Cell line G.3.8 (FIG. 1) is one of the cultures that proliferate rapidly on proliferation medium. According to prior methods it produces no or very few somatic embryos. Cell line G.35.8 (FIG. 2) is one of the cultures that proliferate relatively slowly on proliferation medium. It does produce a few mature somatic embryos according to prior methods. Four different protocols for maturation were tested: A) Maturation for 20 weeks on maturation medium including 40 $\mu$M ABA and 5% PEG-4000 (control method). B) Maturation as for A), but from week 4 to 8 the cultures were matured on medium including 40 $\mu$M ABA and 25 $\mu$M PCIB. C) Maturation for 20 weeks on maturation medium including 40 $\mu$M ABA and 25 $\mu$M PCIB. D) Maturation for 20 weeks on medium including no ABA but 25 $\mu$M PCIB.

FIG. 3 shows the number of well developed mature somatic embryos per petri-dish in cell lines G.3.8 and G.35.8 after 20 weeks of maturation according to the four different maturation protocols describes above.

For the tested embryogenic cell lines of *Abies nordmanniana*, only few mature embryos were formed on the control medium with ABA and PEG (FIGS. 1A, 2A and 3). In most cases, maturation of embryos was initiated in these cultures, but due to proliferation of the surrounding tissue the developing embryos were overgrown and they did not develop further. On medium including both ABA and 25 $\mu$M PCIB, proliferation was reduced and high numbers of embryos developed during maturation (FIGS. 1B 2B and 3). However, the number of well-developed mature embryos was dependent on both the concentration and of the application period of PCIB (FIG. 3). Some of the tested cell lines proliferated very fast whereas other cell lines only proliferated slowly on the maintenance medium. These characteristics were also found when the cell lines were grown on maturation medium, and the rate of proliferation during maturation was strongly cell line dependent. The optimum application of PCIB during maturation was found to be determined partly by the rate of proliferation of the cell line, and therefore a general protocol for the application of PCIB covering all tested cell lines could not be found. For illustration, results are shown for a 'fast' and for a 'slow' proliferating cell line.

Cell line G.3.8 proliferated fast on maintenance medium and on maturation medium including ABA and PEG and no well formed mature embryos developed during maturation on medium without PCIB (FIGS. 1A and 3). When 25 $\mu$M PCIB was included into the medium from week 4 to 8 of the 20 week maturation period, about 40 well formed embryos developed and proliferation was reduced slightly (FIGS. 1B and 3). However, through inclusion of 25 $\mu$M PCIB during the entire maturation period about 125 well-formed embryos developed per Petri dish and proliferation was strongly reduced (FIG. 1C and FIG. 3).

Cell line G.35.8 proliferated slowly on maintenance medium and also during maturation on medium including ABA and PEG. Only few mature embryos developed on the control medium (FIGS. 2A and 3), and inclusion of PCIB into the maturation medium had a clear positive effect on the number of well formed embryos for this cell line. However, best results were found when PCIB was only included into the maturation medium from week 4 to 8 of the 20 week maturation period where about 250 embryos developed per Petri dish (FIGS. 2B and 3). Opposite to cell line G.3.8, inclusion of PCIB during the entire maturation period had a negative effect on the number of well formed mature embryos of cell line G.35.8 (FIGS. 2C and 3) and only about 15 well formed embryos developed per Petri dish.

If ABA was excluded from maturation medium including 25 $\mu$M PCIB, a relatively high number of embryos started to mature in the cultures, but only few and clearly abnormal and precociously germinating embryos were developed on this medium for all tested cell lines (FIGS. 1D and 2D). Since practically no maturation takes place on medium without both anti-auxin and ABA this clearly indicates that anti-auxins in themselves play a role in embryo maturation. As in the other cases of inclusion of PCIB, proliferation was reduced.

FIG. 4 discloses the morphology of mature somatic embryos of Abies nordmanniana and typical abnormalities caused by over-exposure to PCIB during maturation. A: well developed embryo with a straight axis from root to shoot and approximately 5 cotyledons surrounding the shoot meristem. B: embryo with only two cotyledons. The embryo is relatively symmetric around the vertical axis, and the shoot meristem is normally intact. C: embryo with two cotyledons. The embryo is clearly assymetric with a big and a small cotyledon. The shoot meristem is affected by the abnormality. D: embryo with only one cotyledon. The embryo has no functional shoot meristem.

The well developed mature somatic embryo of Abies nordmanniana, has a straight axis from root to shoot pole, and about 5 cotyledons (FIG. 4A). When cell lines were grown on maturation medium including PCIB in supra optimum concentrations or for some cell lines in too long periods, high numbers of abnormal mature embryos developed. A very characteristic abnormality was a reduction in the number of cotyledons (FIG. 4B–D). When the slowly proliferating cell lines were grown on medium containing ABA and 25 $\mu$M PCIB for longer periods than 4 weeks, embryos with only two symmetric cotyledons developed (FIG. 4B). When higher concentrations than 25 $\mu$M of PCIB was used for the tested cell lines, the embryos developed asymmetrically with one major and one minor cotyledon (FIG. 4C) or with only one cotyledon (FIG. 4D). The shoot meristem seemed to be intact in mature embryos with two symmetric cotyledons and these embryos could germinate and develop further, but mature embryos with two asymmetric or only one cotyledon did not germinate properly.

FIG. 5 discloses maturation of cell line G.78.14. This cell line proliferates rapidly and produces very few normal mature embryos according to prior methods. The cell line was matured for 20 weeks on medium comprising 40 $\mu$M ABA and a) 25 $\mu$M PCIB, b) 0.4 mM phloroglucinol, or c) reduced concentration of Boron (20% of normal concentration). For control see FIG. 1a or 2a.

Medium with a decreased concentration of Boron also had a positive effect on the number of mature embryos (FIG. 5). On maturation medium with a decreased concentration of Boron, a clear increase in the number of developing mature embryos was seen in some of the tested cell lines. However, proliferation continued in these cultures and overgrowth of the developing embryos reduced the number of well-developed embryos. As reduced boron was only tested at one concentration it is possible that positive effects could be obtained by optimising the concentration of boron.

When embryo maturation was performed on medium including phloroglucinol (0.4 mM) no well developed embryos were found and proliferation was increased in the tested cell lines (FIG. 5). Phloroglucinol is supposed to act as an inhibitor of auxin degradation and the addition of phloroglucinol is thus supposed to cause an increase in endogenous auxin concentration.

FIG. 6 discloses maturation of cell line G.78.14 for 20 weeks on maturation medium comprising 40 $\mu$M ABA and a) 2.5 mg/L TIBA (5 $\mu$M), or b) 25 mg/L TIBA (50 $\mu$M).

For both of the tested concentrations of the auxin-transport inhibitor, TIBA, a strong reduction of the proliferation on the maturation medium was found for all tested cell lines, but only very few, and mostly abnormal, mature embryos developed (FIG. 6). Since TIBA was only tested in two concentrations (5 and 50 $\mu$M) one cannot exclude the possibility that a positive effect could be obtained with a lower concentration.

FIG. 7 discloses the endogenous concentration of indole acetic acid in three cell lines of Abies nordmanniana. The concentrations were measured during proliferation of the cultures. The bars represent the standard error.

Endogenous IAA was found in proliferating cultures of all 3 tested cell lines (FIG. 7). The concentration of IAA was found to be in the range from 6 to 9 nmol/mg dry weight in the cultures but no significant difference was found between the 'fast proliferating' and the slower proliferating cell line.

The water content of mature zygotic embryos of Abies nordmanniana was about 30%. The water content of mature somatic embryos was genotype dependent, but for both cell lines the water content of somatic embryos were higher than the water content of zygotic embryos. For somatic embryos from maturation medium with PCIB, the water content was between 65 and 75%, which is lower than in the corresponding mature somatic embryos from maturation medium without PCIB.

FIG. 8A discloses germinating embryos produced according to the invention. The embryos have been subjected to cold treatment for two weeks followed by two weeks of germination on germination medium. FIG. 8B discloses germinated plants according to the invention transferred to soil for hardening.

High numbers of mature embryos was developed from several cell lines with the use of PCIB in the maturation medium. Germination of embryos was fine and close to 100% of the embryos developed both shoot and root, and more than 2000 of the plants were transferred to soil and into the greenhouse (FIG. 8B). Regenerated plants were generally dormant as is the case with seedlings of the same species. The plants survived in the soil, but it was very difficult to obtain further growth from the bud. The problem was probably related to dormancy and lately it has been possible to induce further growth by optimisation of the germination protocol. It is known that subjecting such dormant plants to conditions of short days and low temperatures for a period of time to be determined experimentally induces bud flushing and thereby continued growth.

EXAMPLE 2

Maturation in Newly Established *Abies nordmanniana* Embryogenic Cultures

Approximately 50 cell lines were initiated from mature seeds in the same way as cell line G.78.14 (Example 1). The cultures were initiated and maintained on modified half strength BLG medium (See example 1). The cultures were less than 6 months old when they were subjected to maturation.

Protocol

The cultures were plated as described in Example 1. The cultures were subjected to two different maturation protocols.
1) Maturation for 8 weeks on culture medium comprising 40 µM ABA and 5% PEG-4000.
2) Maturation for as 1) but from week 2 to 4 the cultures were on culture medium comprising 40 µM ABA and 25 µM PCIB.

Results:

Preliminary experiments had shown that it was detrimental to subject these newly established cell lines to continuous anti-auxin. Therefore only one treatment comprising a short anti-auxin step was included.

First of all it should be noted that the newly established cell lines require substantially shorter time for maturation than the older cell lines. Part of the cell lines produced high numbers of well developed mature somatic embryos according to the control treatment (treatment 1). The remaining cell lines did not.

When subjected to the two weeks anti-auxin step described above, almost all cell lines produced high numbers of mature somatic embryos according to the invention. Thus the outcome was that it was possible to produce mature somatic embryos from all tested cell lines.

EXAMPLE 3

Maturation in Embryogenic Cultures of *Picea abies*
Plant Material

Three embryogenic cell lines, D.2.9, D.4.1, D.7.1, of *Picea abies*, initiated from immature seeds in 1989 and kept in cryostorage until 1998 as described by Nørgaard et al (1993) were used for the present experiment. The cultures were maintained on semi-solid proliferation medium BMI-S1 (Krogstrup 1986) gelled with 1.8 g/L gelrite by biweekly sub-cultures. Prior to transfer to maturation medium, 4 grams of cell mass from each cell line was weighed off and transferred to 50 ml liquid proliferation medium in a 250 ml Erlenmeyer flask. The flask also contained a sterile magnet.
Pre-treatment To disintegrate the cultures they were stirred for 5 minutes using a magnet stirrer. Then the flasks were shaken for 15 minutes on a rotary shaker at 175 rpm. The medium with suspended cell aggregates were subsequently poured into a 100 ml measuring cylinder and allowed to settle for 30 minutes. The supernatant was discarded and aliquots of 1 ml of cells were plated on sterile Whatman #54 paper discs placed an the various maturation media. Three replicate dishes were made for each combination of cell line and treatment.
Maturation Protocol Five maturation protocols were tested.
A: Maturation on BMG-1 medium (Krogstrup et al 1988) modified by increasing the ABA concentration to 40 µM.
B: As A, but from week 2 to week 4 maturation on culture medium comprising 2.5 µM PCIB and 40 µM ABA.
C: As A, but from week 2 to week 4 maturation on culture medium comprising 5.0 µM PCIB and 40 µM ABA.
D: Maturation on medium comprising 2.5 µM PCIB and 40 µM ABA.
E: Maturation an medium comprising 5.0 µM PCIB and 40 µM ABA.
Results Cell lines D.4.1 and D.7.1 which are typical so-called A-type cell lines produced mature somatic embryos without any anti-auxin step. However, they produced higher numbers of somatic embryos when an anti-auxin step was included. The effect of the anti-auxin step was to reduce the proliferation during maturation.

Cell line D.2.9 does not produce as many embryos as the other two cell lines. When matured without an anti-auxin step, the culture gradually turns brown and looses viability. Mature embryos are then produced. When subjected to an anti-auxin step the culture also initially turns brown, but later new clumps of fine, translucent proliferating embryogenic cell mass is produced at the periphery of the culture. From this cell mass, a high number of mature somatic embryos are in turn produced.

Thus it seems that the inclusion of an anti-auxin step has the effect of changing cell lines that are not capable of producing mature somatic embryos into cell lines that can do this. Clumps of the newly formed cell masses from D2.9 have been transferred back to proliferation medium and in this way it has become possible to produce mature embryos from this culture again.

It is therefore possible to use one aspect of the method according to the invention to improve the ability of cell lines to produce mature somatic embryos. This can evidently be done by subjecting the cultures to the conditions described above for cell line D.2.9, but it can likewise be done by incorporating an anti-auxin step in the proliferation step or in a step between proliferation or maturation.

EXAMPLE 4

Maturation in Embryogenic Cultures of *Picea sitchensis*
Plant Material

Two cell lines of *Picea sitchensis*, G.1.12, G.1.13, initiated from cotyledons from mature embryos were used for the present study. The cultures were initiated and pretreated on BMI-S1 medium as above, but with 1000 mg/L casein hydrolysate and 10 μM 2,4-D.

Pretreatment, maturation medium and anti-auxin step as for *Picea abies*.

Results

Both the tested cell lines produced high numbers of mature somatic embryos both with and without an anti-auxin step. However, proliferation was clearly reduced by subjecting the cultures to an anti-auxin step, and the general appearance of the cultures was improved.

EXAMPLE 5

Transformation of Embryogenic *Abies nordmanniana* Cell Cultures and Subsequent Regeneration of Plants Embryogenic cell lines of *Abies nordmanniana* were transformed biolistically using the method disclosed by Walter et al (1998) with a few modifications. Firstly, the species is *Abies nordmanniana* in stead of *Pinus radiate*. The modified half strength BLG medium described in Example 1 above was used for proliferation and also during the selection step after transformation.

The plasmid transferred was the pCW 122 plasmid containing the reporter gene uidA under the control of the CaMV 35S promoter and the npt II selectable marker gene controlled by the CaMV 35S promoter.

Selection was carried out on proliferation medium comprising 50 mg/L geneticin. Expression of the uidA reporter gene was detected histochemically in transformed embryogenic tissue, in derived mature somatic embryos produced according to the present invention and in regenerated plants likewise produced according to the present invention using GUS staining.

EXAMPLE 6

Maturation of *Abies nordmanniana* Cell Lines Comprising an Auxin Phase

Three protocols were used for maturation of the cell lines:
A) Maturation on culture medium comprising 40 μM ABA and 5% PEG-4000 (control).
B) As A) but culture medium comprising 40 μM ABA and 25 μM PCIB from week 2 to week 4.
C) as B) but culture medium comprising 40 μM ABA and 5 μM IAA from week four.

Embryos produced according to protocol C were longer than embryos produced according to protocol B. The overall quality of these embryos was also higher than the quality of the embryos according to protocol B.

EXAMPLE 7

Maturation of *Abies nordmanniana* Cell Lines Comprising a Shift From Maltose to Sucrose as Carbohydrate Source During the Last Period (the Third Phase) of the Maturation Period Except from the carbohydrates, the basic maturation medium was composed as described for the control in example 1. However, PCIB was included in a prior determined optimum concentration and period for each of the tested cell lines. Four treatments with different combinations of carbohydrates were tested during maturation:
A) Maturation on culture medium comprising 45 g/L sucrose as carbohydrate source during the entire maturation period.
B) Maturation on culture medium comprising 45 g/L maltose as carbohydrate source during the entire maturation period. Typical embryo from the treatment is disclosed in the left picture of FIG. 9.
C) Maturation on culture medium with 45 g/L maltose during the first part of the maturation period, followed by a shift to maturation medium comprising 22.5 g/L sucrose and 22.5 g/L maltose during the last two weeks of the maturation period. Typical embryo from the treatment is disclosed in the right picture of FIG. 9.
D) Maturation on culture medium with 45 g/L maltose during the first part of the maturation period, followed by a shift to maturation medium comprising 45 g/L sucrose as carbohydrate source for the last two weeks of the maturation period. Typical embryo from the treatment is disclosed in the center picture of FIG. 9.

Results

When sucrose was used as carbohydrate source during the entire maturation period (treatment A), no well developed mature embryos were produced. All produced mature embryos showed pronounced abnormalities. When maltose was used as the sole carbohydrate source during the entire maturation period (treatment B), high numbers of embryos were produced (as in FIGS. 1C and 2B). The mature embryos were well shaped, but for most cell lines the embryos were small compared to mature zygotic embryos.

When the cells were transferred from maturation medium with maltose to a maturation medium including sucrose during the last two weeks of maturation (treatment C and D), a clear increase in the size of the mature embryos was observed (FIG. 9). A shift to medium including 45 g/L of sucrose (treatment D) resulted in the development of mature embryos with a size resembling the size of zygotic embryos of *Abies nordmanniana*. The average fresh weight of mature embryos from treatment B) was about 50 mg compared to an average fresh weight of mature embryos from treatment D) of about 120 mg per embryo. An additional effect of treatment D) compared to treatment B) was, that the maturation period was reduced with about four weeks. The observed effect of a shift from maltose to sucrose during the last part of the maturation period was surprising and unexpected, because prior investigations has reported a clear negative effect of sucrose during maturation of somatic embryos from *Abies nordmanniana* (Plant science vol 124:211–221, NØRGAARD) and for other conifer species (U.S. Pat. No. 5,187,092 INSTITUTE OF PAPER SCIENCE AND TECHNOLOGY).

It is expected, that components of the metabolisable carbon sources, and more specifically carbohydrate sources generally will achieve the unexpected maturation effect. One could suggest components as lactose, fructose, glucose, maltotriose, starch, galactose or mixtures thereof. Especially fructose and glucose alone or mixtures there between has indicated similar positive effects on the mature embryos. The culture medium has a content of between 1 and 100 g/L of fructose or glucose.

LIST OF REFERENCES von Arnold S, Egertsdotter U, Ekberg I, Gupta P, Mo H, Nørgaard, J, 1995, "Somatic embryogenesis in Norway spruce (*Picea abies*)", In: Somatic embryogenesis in woody plants, vol 3 (eds S Jain, P Gupta, R Newton), Kluwer Academic Publishers, pp 17–36.

Aitken-Christie J, Parkes B D, 1996, "Improved embryogenesis process for initiation and maturation", PCT-application, published as WO96/37096.

Attree S M, Fowke L C, 1993, "Maturation, desiccation, and encapsulation of gymnosperm somatic embryos", PCT-application, published as WO93/11660.

George E F, 1993, "Plant Propagation by Tissue Culture, Part 1, The Technology", Execetics Ltd, 2$^{nd}$ Edition.

Krogstrup P, 1986, "Embryolike structures from cotyledons and ripe embryos of Norway spruce (*Picea abies*)", Can. J. For. Res. vol. 16:664–668.

Krogstrup P, Eriksen E N, Møller J D, Roulund H, 1988, "Somatic embryogenesis in Sitka spruce (*Picea sitchensis* (Bong.) Carr.)", Plant Cell Rep. vol. 7:594–597.

Murashige T, Skoog F, 1962, "A revised medium for rapid growth and bio-assays with tobacco tissue cultures", Physiol Plant vol.15:473–497.

Nørgaard J V, 1997, "Somatic embryo maturation and plant regeneration in *Abies nordmanniana* Lk.", Plant Science vol 124:211–221.

Nørgaard J V, Krogstrup P, 1991, "Cytokinin induced somatic embryogenesis from immature embryos of *Abies nordmanniana* Lk.", Plant Cell Rep vol 9:509–513.

Nørgaard J V, Duran V, Johnsen Ø, Krogstrup P, Baldursson S, von Arnold S, 1993, "Variations in cryotolerance of embryogenic *Picea abies* cell lines and the association to genetic, morphological and physiological factors", Can J For Res 23:2560–2567.

Nørgaard J V, Krogstrup P, 1995, "Somatic embryogenesis in Abies spp", Somatic embryogenesis in Woody Plants, Eds S Jain, P Gupta, R Newton, vol 3:341–355.

Paques M, Bercetche J, 1999, "Procede de rajeunissement de gymnospermes par embryogenese somatique", PCT-application, published as WO99/23874.

Roberts D R, Flinn B S, Webb D T, Webster F B, Sutton B C S, 1990, "Abscisic acid and indole-3-butyric acid regulation of maturation and accumulation of storage proteins in somatic embryos of interior spruce", Physiol. Plant. Vol 78:355–360.

Schenck R U, Hildebrandt A C, 1972, "Medium and techniques for induction and growth of monocotyledonous and dicotyledonous plant cell cultures", Can. J. Bot. vol. 50:199–204.

Smith D R, 1996, "Growth medium", U.S. Pat. No. 5,565,355, issued 15, Nov. 1996.

Uddin M R, 1993, "Somatic embryogenesis in gymnosperms", U.S. Pat. No. 5,187,092, issued 16, Feb. 1993.

Verhagen S A, Wann S R, 1989, "Norway spruce somatic embryogenesis: High frequency initiation from light-cultured mature embryos", Plant Cell Tiss. Org. Cult. vol. 16:103–111.

Walter C, Grace W, Wagner A, White D W R, Walden A R, Donaldson S S, Hinton H, Gardner R C, Smith D R, 1998, "Stable transformation and regeneration of transgenic plants of *Pinus radiata* D. Don", Plant Cell Reports 17:460–468.

What is claimed is:

1. A method for maturation of conifer somatic embryos, comprising
an anti-auxin step, where an embryogenic cell mass is cultured with a culture medium comprising an anti-auxin.

2. A method according to claim 1, further comprising a second step before the anti-auxin step, where the embryogenic cell mass is cultured with a culture medium.

3. A method according to claim 1, further comprising a third step after the anti-auxin step where the embryogenic cell mass is cultured with a culture medium essentially free of anti-auxin.

4. A method according to claim 1, whereby the anti-auxin step lasts from 2 days to 50 weeks.

5. A method according to claim 2, whereby the second step before the anti-auxin step lasts from two days to 10 weeks.

6. A method according to claim 3, whereby the third step after the anti-auxin step lasts from two days to 40 weeks.

7. A method according to claim 1, whereby the culture medium in at least one of the steps further comprises a maturation agent.

8. A method according to claim 7, whereby the culture medium of all the steps further comprises at least one maturation agent.

9. A method according to claim 7, whereby the maturation agent is selected from the group comprising abscisic acid, silver nitrate, jasmonic acid, abscisyl alcohol, acetylenic aldehyde, dihydroacetylenic alcohol, phaseic acid, dihydrophaseic acid, 6'-hydroxymethyl abscisic acid, beta-hydroxy abscisic acid, beta-methylglutaryl abscisic acid, beta-hydroxy-beta-methylglutarylhydroxy abscisic acid, 4'-desoxy abscisic acid, abscisic acid, beta-D-glucose ester, 2-2(2-p-chlorophenyl-transethyl-cyclopropane carboxylic acid.

10. A method according to claim 7, whereby the maturation agent is abscisic acid at a concentration of between 0.1 and 200 μM.

11. A method according to claim 1, whereby the anti-auxin is selected from the group consisting of α-(1-naphtylmethyl-sulfide)-isobutyric acid, α-(1-naphtylmethyl-sulfide)-propionic acid, α-(2-naphtylmethyl-sulfide)-isobutyric acid, α-(2-naphtylmethyl-sulfide)-propionic acid, δ-(naphtylmethyl-selenide)-η-valeric acid, (-)-α-(2,4,5-trichlorophenoxy)-propionic acid, (-)-α-(2,-4-dichlorophenoxy)-propionic acid, (-)-α-(2-naphthoxy)-propionic acid, (+)-α-(1-naphthoxy)-propionic acid, (3-phenyl, 1,2,4-thiadiazol-5-yl)thioacetic acid (PTAA), β-naphthalene acetic acid (β-NAA), γ-phenylbutyric acid, 1-(naphthylmethyl-sulfide)-propionic acid, 1-naphthylmethyl-selenidacetic acid, 2-(naphthylmethyl-sulfide)-propionic acid, 2-(o-chlorophenoxy)-2-methylpropionic acid, 2,3,4,5,6-pentachlorophenoxyisobutyric acid, 2,3,5-tri-iodobenzoic acid (TIBA), 2,4,5-trichlorophenoxyisobutyric acid, 2,4,6-trichlorophenoxyacetic acid (2,4,6-T), 2,4,6-trichlorophenoxyisobutyric acid, 2,4-dichloroanisole (2,4-DCA), 2,4-dichlorophenoxyisobutyric acid (2,4-DCIP), 2,4-dihlorophenylsulfoneacetic acid, 2,4-dichlorophenylsulfoxideacetic acid, 2,6-dichlorophenoxyacetic acid, 2-chlorophenoxyisobutyric acid, 2-naphtylmethyl-selenidacetic acid, 3-chlorophenoxyisobutyric acid, 3-indoleisobutyric acid, 3-nitro-4-flourobenzoid acid, 4-chlorophenoxyisobutyric acid, 5-methyltryptophan, 7-aza-indol, 9-hydroxyfluorene-9-carboxylic acid (HFCA), ferulic acid, flavonoids, indoleisobutyric acid, kaempferol, maleic hydrazide, naptalam (N-1-naphtylphthalamic acid), p-Chlorophenoxyisobutyric acid (PCIB), p-coumaric acid, phenoxyacetic acid, phenoxyisobutyric acid, phenylpropionic acid, quercitin, and trans-cinnamic acid.

12. A method according to claim 1, whereby the anti-auxin is PCIB concentration between 0.01 and 200 μM.

13. A method according to claim 1, whereby the anti-auxin is PCIB at a concentration between 1 and 50 μM.

14. A method according to claim 1, whereby the conifer is a member of the *Pinaceae*.

15. A method according to claim 1, whereby the conifer is selected from the genera Pinus, Picea, Abies, Larix and Pseudotsuga.

16. A method according to claim 1, whereby the conifer is an Abies sp.

17. A method according to claim 1, whereby the conifer is a Picea sp.

18. A method according to claim 1, whereby the conifer is an Abies sp and the anti-auxin is PCIB at a concentration between 1 and 100 µM.

19. A method according to claim 1, whereby the conifer is a Picea sp and the anti-auxin is PCIB at a concentration between 0.1 and 50 µM.

20. A method according to claim 3, whereby the culture medium used during at least part of the third step after the anti-auxin step further comprises an auxin.

21. A method according to claim 3, whereby the embryogenic cell mass is cultured with a culture medium comprising a carbohydrate source.

22. A method according to claim 21, where the embryogenic cell mass is cultured with a culture medium comprising sucrose, fructose, or glucose.

23. A method according to claim 21, whereby the culture medium has a content of between 1 and 100 g/L of metabolisable carbon sources.

24. A method according to claim 21, whereby the further culturing is performed for a period of from 2 days to 10 weeks.

25. A method according to claim 1 where the conifer is *Abies nordmanniana*.

26. A method according to claim 1 where the conifer is *Picea abies* or *Pichea sitchensis*.

* * * * *

UNITED STATES PATENT AND TRADEMARK OFFICE
CERTIFICATE OF CORRECTION

PATENT NO. : 6,897,065 B1
DATED : May 24, 2005
INVENTOR(S) : Jens Iver Find

It is certified that error appears in the above-identified patent and that said Letters Patent is hereby corrected as shown below:

<u>Column 18,</u>
Line 16, delete "abscisic acid, beta-D-glucose ester" and insert -- abscisic acid beta-D-glucose ester --.
Line 17, delete "2-2(2-p-chlorophenyl-transethyl-cyclopropane carboxylic" and insert -- 2-2(2-p-chlorophenyl-transethyl)-cyclopropane carboxylic --.
Line 56, after "PCIB" insert -- at a --.

Signed and Sealed this

Second Day of May, 2006

JON W. DUDAS
*Director of the United States Patent and Trademark Office*